(12) United States Patent
Markov

(10) Patent No.: US 6,169,963 B1
(45) Date of Patent: Jan. 2, 2001

(54) MAGNETIC FIELD STRENGTH MAPPING SYSTEM

(75) Inventor: Marko Markov, Boca Raton, FL (US)

(73) Assignee: Magnetherapy, Inc., Riviera Beach, FL (US)

( * ) Notice: Under 35 U.S.C. 154(b), the term of this patent shall be extended for 0 days.

(21) Appl. No.: 09/088,931

(22) Filed: Jun. 2, 1998

(51) Int. Cl.$^7$ ........................................ A61B 5/05
(52) U.S. Cl. .................. 702/57; 702/115; 324/319; 600/409; 600/425
(58) Field of Search .................. 702/57, 115, 116; 324/319–322, 172–174; 600/407, 409, 425

(56) References Cited

U.S. PATENT DOCUMENTS

| | | | |
|---|---|---|---|
| 4,197,855 | * | 4/1980 | Lewin .................................. 600/409 |
| 4,223,228 | * | 9/1980 | Kaplan ................................ 324/207.2 |
| 4,902,975 | * | 2/1990 | Kess .................................... 324/318 |
| 4,949,044 | * | 8/1990 | Starewicz et al. .................. 324/320 |
| 5,113,424 | * | 5/1992 | Burdea ................................ 600/425 |
| 5,313,164 | * | 5/1994 | Starewicz et al. .................. 324/318 |
| 5,493,517 | * | 2/1996 | Frazier ................................ 702/33 |

* cited by examiner

Primary Examiner—Marc S. Hoff
Assistant Examiner—Bryan Bui
(74) Attorney, Agent, or Firm—McHale & Slavin

(57) ABSTRACT

The instant invention is directed toward a method and an apparatus for mapping the magnetic field strength or flux density of a magnetic source. The invention provides a robotically controlled sensor which is moved in a controlled manner throughout an area of flux density and the variations in the flux density are recorded. The position and recorded magnetic field strength at numerous points throughout the test area are recorded and the data is assembled into a graphical representation the end result of which is a multi-dimensional mapping of the magnetic field strength as a function of distance from the source. The testing method and apparatus provide a convenient methodology for accurately determining dosimetry and tissue penetration of therapeutic magnetic devices.

12 Claims, 3 Drawing Sheets

MAGNETIC FIELD STRENGTH MAPPING SYSTEM

FIELD OF THE INVENTION

This invention relates to the field of bioelectromagnetic technology and particularly relates to a method and apparatus for testing magnetic field strength and tissue penetration of a magnetic field and for accurately describing the field strength in a multi-dimensional representation.

BACKGROUND OF THE INVENTION

The increasing interest toward alternative and complimentary medicine has attracted the attention of scientists and clinicians to the potential benefit of using magnetic field (MF) for therapeutic purposes. At present, magnetic and electromagnetic fields are widely accepted as real physical entities existing in the environment. Scientists and medical practitioners acknowledge that the use of magnetic field therapy for the treatment of various pathologies represents an effective and non-invasive method to directly treat various injuries, including pain and inflammation.

A rigorous scientific approach toward the clinical application of magnetic fields was suggested and developed in the last several decades, mainly in Europe and Asia. Both static and time varying magnetic fields were successfully applied to treat therapeutically resistant problems in the musculoskeletal system.

However, despite a long history of interest on the part of scientists and clinicians, very little is known about the mechanisms of action provided by magnetic therapy. Therefore the clinical application of magnetic fields is very limited and unpredictable. The ability to duplicate or determine magnetic field strength is currently more of an art than a science.

After World War II, Japan, later Romania and the former Soviet Union, developed various aspects of magnetic therapy. In Japan therapeutic devices using magnets are registered under the Drug Regulation Act of 1961 as #81 and by 1976 such devices were in common use in Japan, mainly due to the efforts of Kyochi Nakawa. Therapeutic devices using magnets have also had a long history in Europe. Between 1960–1985 most European countries had produced therapeutic devices using magnets. The first clinical application of magnetic therapeutic devices in the USA, utilizing electromagnetic stimulation, occurred in 1974. The first book on dealing with the use of therapeutic magnetic devices, written by N. Todorov, was published in Bulgaria in 1982 covering the use of magnets for treatment of more than 2700 patients with 33 different pathologies. In recent years numerous studies have demonstrated that permanent magnetic fields can have a profound effect on a number of biological processes. Most recently it has been recognized that magnetic field energy can modify many physiological processes ranging from cellular and membrane functioning to alterations in the mechanical properties of important tissues and organs. The use of both permanent magnets and electromagnetic fields for the treatment of musculoskeletal injuries and pathologies have opened new avenues in both human and veterinary medicine.

Presently, there is no coordinated effort on the part of the scientific community to create dosimetry and methodology for the quantification of this type of stimulation. Saying that a patient was "magnetically stimulated" is thus as nonspecific as saying a patient was given a drug. It should be made clear that magnetic field stimulation requires as precise a control of dosage as any other therapy. This dosage is even more complicated since it needs to take into account a number of physical parameters which characterize any magnetic field generating system.

In general, electromagnetic (EMF) therapeutic modalities can be categorized in five groups:
  permanent magnetic fields;
  low frequency sine waves;
  pulsed electromagnetic fields (PEMF);
  pulsed radiofrequency fields (PRF); and
  transcranial magnetic stimulation.

Permanent magnets provide a practical non-invasive method for stimulation of cells and tissues. This stimulation results in an acceleration of the healing process which is believed to result from enhanced tissue repair and regeneration.

Magnetic and electromagnetic fields can be used for the treatment of various musculoskeletal injuries and pathologies which occur due to injury, over-use of a particular body part, or the effects of illness or infection. The most effective applications of permanent magnets are related to bone unification, wound healing and the reduction of pain and inflammation.

As the ability of magnetic fields to modulate biological responses has become more widely accepted, the need for an accurate and effective device to quantify the various magnetic field parameters as they interact with the targeted tissue is critical. If a serious scientific approach is to be taken in developing this methodology, it is not enough to merely cite anecdotal evidence of utility. It is imperative that researchers be provided with a tool which enables them to develop universally accepted data regarding dosimetry and methodology whereby an organized progression and development of the science is made possible.

Most of the permanent magnets available in the market purport to have an unrealistically high magnetic field characteristics. Several companies use the term gauss rating to characterize the strength of their products. This term is misleading, since gauss rating may be used to characterize the magnet itself, but not the external magnetic field. In actuality, the magnetic field strength exerted at close proximity to the surface of the magnet is 4–10 times smaller than the gauss rating of the magnet.

The most biologically and clinically relevant characteristic of the magnetic field is the field strength at the target site. This means that the ability to quantify the complete three-dimensional dosimetry of the magnetic field is extremely important in order to analyze and further predict the biological effects at a given target, having a defined biological and/or clinical status.

It must be emphasized that the expected therapeutic results strongly depend on the magnetic field strength at the target tissue. Therefore, a mere knowledge of the gauss rating and even the field strength at the surface of the magnet is insufficient if one is to predict expected therapeutic effects at the target site.

Thus, what is lacking in the art is a method and apparatus which is capable of determining magnetic field strength in real time and at the tissue location for which treatment is desired.

SUMMARY OF THE INVENTION

The invention is directed toward a process and apparatus for analyzing a source of magnetic field strength so as to accurately define the effective geometry of the generated magnetic field and quantify the strength of the field which is generated at the tissue site. In order to establish a reliable physical method for the evaluation of a three-dimensional structure of the magnetic field, a robotically controlled gauss metering system has been designed. The system utilizes a gauss meter for measuring the magnetic field strength or flux density. The gauss meter is coupled to a robotic arm which is capable of movement along the X,Y and Z axis. The robotically controlled gauss meter is moved through a pre-programmed series of stepwise movements. Data regarding the flux density is collected at each point, and the data is fed to a program which creates a multi-dimensional image, e.g. a two or three dimensional mapping, that approximates the shape and strength of the detected magnetic field.

Thus it is an objective of the present invention to provide an apparatus for detecting and evaluating the magnetic field strength of a given source of magnetic flux in multiple dimensions.

It is a further objective of the instant invention to provide a graphical representation of the detected flux density at varying distances and positions relative to the source of magnetic energy.

It is yet another objective of the instant invention to teach a method of quantifying the magnetic field strength at a given location within affected tissue so as to provide for quantification of the therapeutic magnetic effect being applied thereto.

Other objectives and advantages of the present invention will become apparent to those skilled in the art from the following detailed description when read in conjunction with the accompanying drawings.

DETAILED DESCRIPTION OF THE INVENTION

Figure 1:
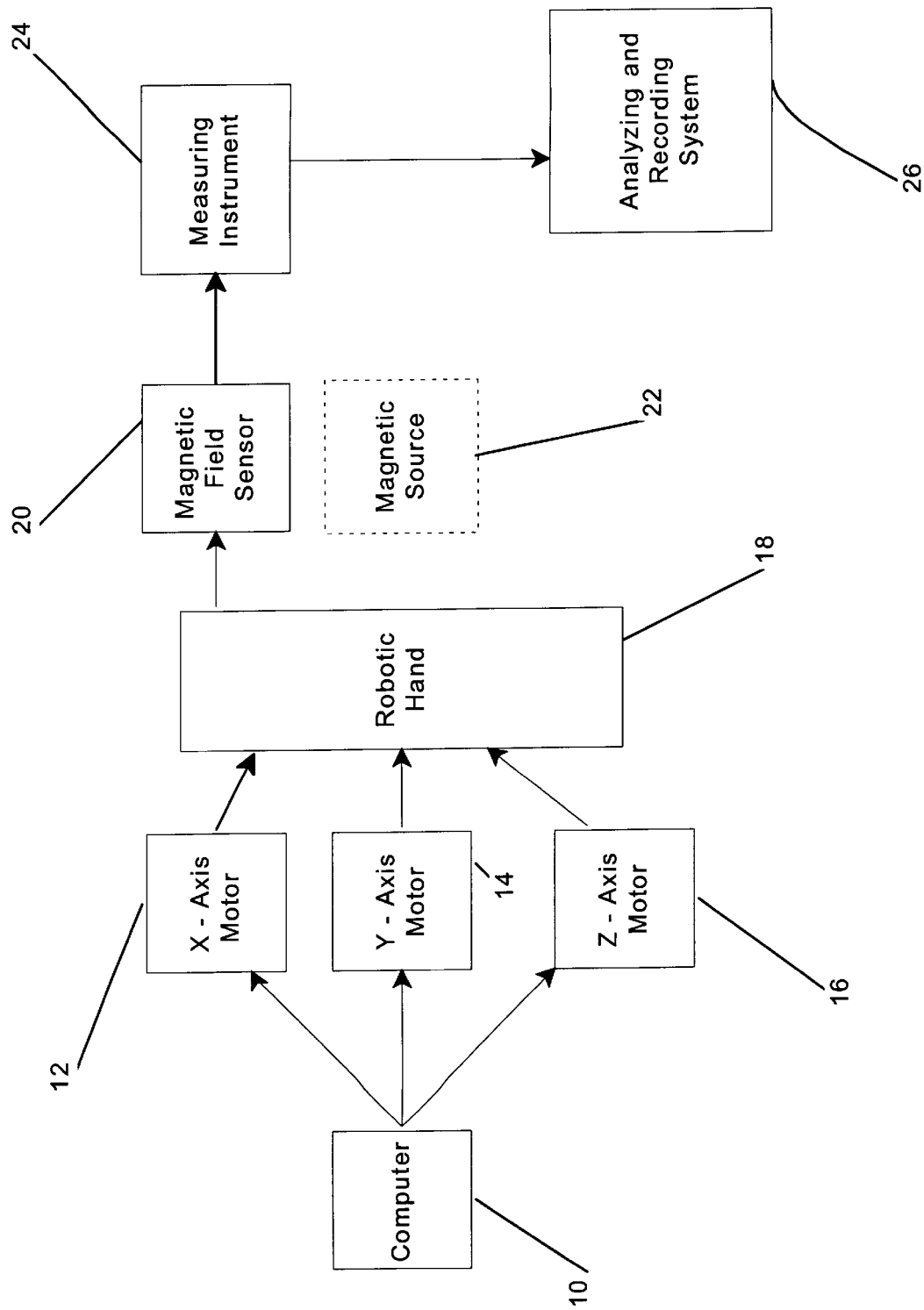
FIG. 1 is block diagram which illustrates the interaction and arrangement of the components of the instant magnetic field strength mapping system.

Referring to FIG. 1, a computer 10 is programmed so as to generate position coordinates having an X,Y and Z value. These coordinates are then transmitted to positioning motors for the X-axis 12, Y-axis 14 and Z-axis 16. These motors, which are DC stepper motors, typically have a velocity of about 25,000 steps per revolution and a position range of from 0–99,999,999 steps. The motors independently control motion in the three respective directions for defining the position of a robotic arm 18. The robotic arm supports a magnetic field strength determining sensor 20, in an area adjacent to the source of magnetic field strength 22. In a preferred embodiment the sensor is a flat Hall effect probe having dimensions of approximately 2 mm×3 mm. The probe is encapsulated in a holder which is approximately 8 cm in length, 1 cm in width and 3 mm in height. The sensor 20 is electrically coupled to a measuring instrument 24 which is an adjustable gauss meter preferably having a digital output which indicates the magnetic field strength determined by the sensor. The measuring instrument is further connected to an analyzing and recording system 26 which is a software program designed to enable the user to input a requisite number of strategic locations and correlate this positional information with the magnetic field strength determined at that location. The positional field strength readings are stored for each individual slice or cut as the sensor is first moved throughout the prescribed area in an X-Y plane for a given value of Z and then the sensor is moved in the Z direction so as to define a new X-Y plane, and the process is repeated. The various slices are methodically moved through as the computer first records the data as it is gathered by the sensor and then arranges it so that a graphical representation can be generated in the form of a multi-dimensional map which links together the various slices of information relating to the magnetic field strength at varying distances from the source of said magnetic field. Since the penetration of a static magnetic field in air is equivalent to the penetration of such a field through biologic material, the map thus generated is indicative of tissue penetration. Thus, an accurate and repeatable methodology is provided for quantifying the dosimetry at the tissue location for which treatment is desired.

Figure 2:
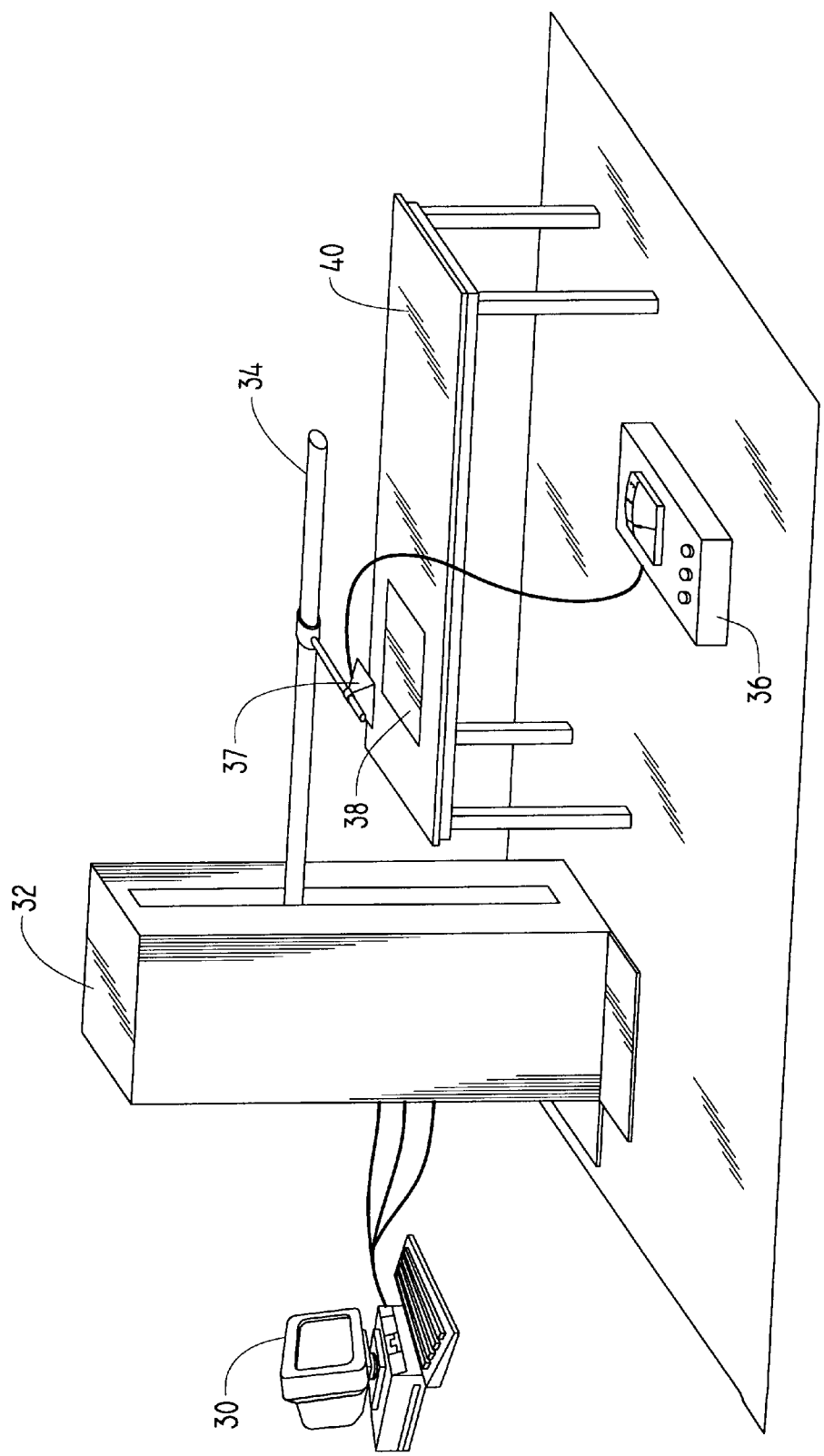
FIG. 2 is a pictorial view of the robotically controlled magnetic field strength mapping system.

Referring now to FIG. 2, a computer 30 is shown attached to a computer-aided motor driven robotic arm device 32. In a preferred embodiment, a COMPUMOTOR which is available from the Parker Hannifin Corporation is utilized.

A computer software program was designed to command independent movement of the robotic arm along any one of the X,Y,Z axes. The robotic arm is mechanically coupled to a sensor retaining arm 34. The sensor retaining arm is adapted to retain one, or possibly a plurality, of magnetic field strength sensors or probes 37, which are used to determine the magnetic field strength and which are electrically coupled to a magnetic field strength indicator 36 for registering the determined magnetic field strength. In a preferred embodiment, a kilogaussmeter, model IDR-329 (available from Integrity Design and Research Corporation) with 4 ranges of measurements (0–2, 0–200, 0–2000, 0–20000 G) was incorporated into the system. The sensor retaining arm suspends the sensor in an area adjacent the source of magnetic field strength, typically a permanent magnet 38, which is supported on a non-metallic support surface, e.g. table 40.

By utilization of the robotic arm and software commands issued from the computer it is possible to provide movement along a given axis which can be performed automatically at a given speed and a given step (down to 1 mm). It is also possible to design the program so that after every movement, a pause of several seconds is introduced in order to permit the manual collection of data. Alternatively, the probe could be articulated by hand. Whether movement is manual or automatic, the line movement (for example along the X-axis) may be followed with a small step on the Y-axis, and then the scanning will go along the X-axis in the reverse direction. Once a scanning of the X/Y plane is complete, the system will be moved to the next plane (causing a step in the Z-direction) and so on, until the required slicing is completed. In a preferred embodiment, the data gathered by the probe may be simultaneously transmitted to the computer and the data analyzed and assembled so as to generate a graphical representation or map of the measured magnetic field strength as a function of the position of the probe relative to the magnetic source.

Figure 3:
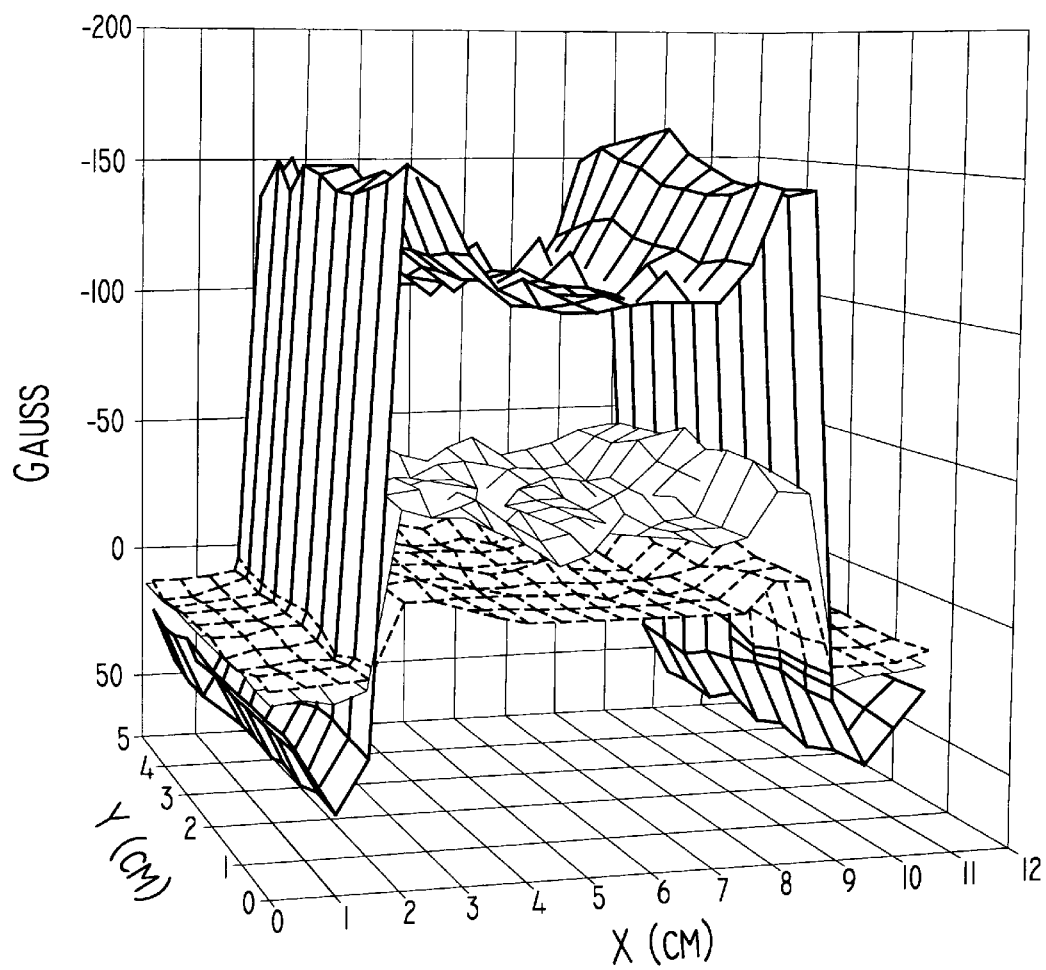
FIG. 3 is a three-dimensional graphical representation approximating the relative shape and strength of a magnetic field at varying distances from the source of the magnetic field.

Referring now to FIG. 3, a graphical representation of the magnetic field strength distribution is presented. For purposes of this representation a permanent magnetic strip, having a magnetic field strength at its surface of approximately 150 gauss and a rectangular shape having dimensions of 5 cm×9 cm, was placed on the non-metallic support surface. The particular magnetic strip used for this test is a TECTONIC® unipolar Flex II magnet which is available from Magnetherapy Inc.. The probe was moved through the X-Y plane in 2 mm steps at distances (Z values) of 0 cm, 2.0 cm and 3.5 cm from the surface of the magnet. At a distance of 0 cm, e.g. right at the surface of the magnet, the field strength is close to the maximum value of the magnet, although some variation is demonstrated across the surface. At a Z value of 2.0 cm, the value drops off to approximately 35% of its surface value. At a Z value of 3.5 cm, the value drops off to virtually zero. By utilizing the method and apparatus of the instant invention it will become clearly evident to a skilled clinician, as to what type of magnetic field strength can be expected at varying tissue depths. This allows the testing of magnetic therapeutic devices to be advantageously conducted with a very high degree of reproducibility.

This can further be described as a method for determining the depth of tissue penetration of a magnetic field wherein (1) a non-metallic support device is provided upon which a magnetic field strength source is positioned; (2) at least one magnetic field strength determining device is located in an area adjacent to the magnetic source, the determining device being electrically coupled with an indicator device for registering the determined magnetic field strength; (3) the determining device is maneuvered to a series of strategic locations which are coplanar and are within the aforementioned area while the magnetic field strength data is simultaneously recorded as a function of position and distance from the magnetic source; (4) the distance of the probe from the magnetic source is altered one or more times and the maneuvering step is repeated after each alteration in distance; and (5) the data is compiled and a multi-dimensional map approximating the depth of tissue penetration and magnetic field strength as a function of the depth is generated. In a particular embodiment the determining device may be placed in a retention device that is designed to removably grasp the determining device. Additionally, the maneuvering step may further include the provision of a movement controlling device which is coupled to the retention device for providing independent movement of the magnetic field strength determining device in the X,Y and Z axes. The maneuvering step may additionally include the provision of an automated position coordinate generator which transmits X,Y,Z coordinate containing positioning commands to the movement controlling device and enables the device to be automatically maneuvered to a series of strategic locations. In various embodiments the operator may choose to display the output in two or three dimensions.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown in the drawings and described in the specification.

I claim:

1. A method for determining the depth of tissue penetration of a magnetic field comprising:
   providing a non-metallic support means;
   positioning a magnetic field strength source on said support means;
   locating at least one magnetic field strength determining means in an area adjacent to said magnetic source, said determining means being electrically coupled with an indicator means for registering the determined magnetic field strength;
   maneuvering said determining means to a series of strategic locations which are coplanar and are within said area while recording the magnetic field strength data as a function of position and distance from the magnetic source;
   altering the distance of said probe from said magnetic source and repeating said maneuvering step; and
   compiling the recorded data; whereby a multi-dimensional map approximating the depth of tissue penetration and magnetic field strength as a function of said depth is generated.

2. The method according to claim 1 wherein said locating of the determining means further includes:
   placing said determining means in a retention means constructed and arranged so as to removably grasp said at least one determining means.

3. The method according to claim 2 wherein said maneuvering step further includes:
   providing a movement controlling means coupled to said retention means for providing independent movement of said magnetic field strength determining means in the X,Y and Z axes.

4. The method according to claim 3 wherein said maneuvering step additionally includes:
   providing an automated position coordinate generator constructed and arranged for transmitting X,Y,Z coordinate containing positioning commands to said movement controlling means; and
   automatically maneuvering said movement controlling means to said series of strategic locations.

5. The method according to claim 1 wherein the multi-dimensional map is two-dimensional.

6. The method according to claim 1 wherein the multi-dimensional map is three-dimensional.

7. A method for mapping magnetic field strength comprising:
   providing a non-metallic support means;
   positioning a magnetic field strength source on said support means;
   locating at least one magnetic field strength determining means in an area adjacent to said magnetic source, said determining means being electrically coupled with an indicator means for registering the determined magnetic field strength;
   maneuvering said determining means to a series of strategic locations which are coplanar and are within said area while recording the magnetic field strength data as a function of position and distance from the magnetic source;
   altering the distance of said probe from said magnetic source and repeating said maneuvering step; and
   compiling the recorded data; whereby a multi-dimensional map approximating the magnetic field strength as a function of position and distance from the magnetic source is generated.

8. The method according to claim 7 wherein said locating of the determining means further includes:
   placing said determining means in a retention means constructed and arranged so as to removably grasp said at least one determining means.

9. The method according to claim 8 wherein said maneuvering step further includes:

providing a movement controlling means coupled to said retention means for providing independent movement of said magnetic field strength determining means in the X,Y and Z axes.

10. The method according to claim 9 wherein said maneuvering step additionally includes:

providing an automated position coordinate generator constructed and arranged for transmitting X,Y,Z coordinate containing positioning commands to said movement controlling means; and automatically maneuvering said movement controlling means to said series of strategic locations.

11. The method according to claim 7 wherein the multi-dimensional map is two-dimensional.

12. The method according to claim 7 wherein the multi-dimensional map is three-dimensional.

* * * * *